United States Patent [19]
Hörold et al.

[11] Patent Number: 6,090,968
[45] Date of Patent: Jul. 18, 2000

[54] PROCESS FOR PREPARING PHOSPHINIC ESTERS

[75] Inventors: Sebastian Hörold, Erftstadt; Norbert Weferling; Heinz-Peter Breuer, both of Hürth, all of Germany

[73] Assignee: Clariant GmbH, Frankfurt, Germany

[21] Appl. No.: 09/342,772

[22] Filed: Jun. 29, 1999

[30] Foreign Application Priority Data

Jun. 29, 1998 [DE] Germany .................... 198 28 863

[51] Int. Cl.⁷ .................................................. C07F 9/32
[52] U.S. Cl. .................. 558/137; 524/133; 558/108; 558/110; 558/177; 558/179; 558/105
[58] Field of Search .................. 558/105, 108, 558/110, 137, 177, 179

[56] References Cited

U.S. PATENT DOCUMENTS 5,973,194  10/1999  Weferling et al. .................. 562/8

*Primary Examiner*—Michael G Ambrose
*Attorney, Agent, or Firm*—Scott E. Hanf

[57] ABSTRACT

The present invention relates to a process for preparing phosphinic esters which comprises a) reacting elemental yellow phosphorus with alkyl halides in the presence of alkali metal hydroxide or alkaline earth metal hydroxide to form a mixture which comprises as main constituents the alkali metal salts and/or alkaline earth metal salts of alkylphosphonous acid, phosphorous acid and hypophosphorous acid b) removing the alkylphosphonous acid from the mixture obtained as described in a), c) esterifying the alkylphosphonous acid, d) adding the resultant ester of the alkylphosphonous acid to a compound having at least one C=C double bond.

The invention likewise relates to the use of the phosphinic esters prepared by this process inter alia as flame retardants and as precursor for further syntheses.

27 Claims, No Drawings

PROCESS FOR PREPARING PHOSPHINIC ESTERS

BACKGROUND OF THE INVENTION

Phosphinic esters are valuable synthesis building blocks and can be used, for example, for preparing polymers and plastics in order to obtain low-flammability materials.

Thus, DE 26 52 007 A1 describes low-flammability epoxy resins by incorporation of carboxy-phosphinic acids. U.S. Pat. No. 5,399,428 A1 describes flame-resistant linear polyesters by incorporation of carboxy-phosphinic acids.

DE 25 40 283 A1 describes the addition of phosphines to α,β-unsaturated carboxylic acids in the presence of aqueous hydrochloric acid and subsequent oxidation.

DE 28 49 003 describes the preparation of phosphorus-containing cyanohydrin derivatives by addition of phosphonous esters to acrolein cyanohydrin derivatives.

Phosphinic esters are obtained by adding phosphonous monoesters to 1-olefins in the presence of peroxide catalysts. However, the yields are only low. The addition of phosphonous monoesters to activated double bonds in the presence of alkoxides as catalyst proceeds better. Suitable unsaturated compounds are α,β-unsaturated carboxylic esters or carbonitriles, α,β-unsaturated ketones and alkyl vinyl sulfones and vinyl acetate (Houben-Weyl, Volume 12/1, pp. 258–259).

The phosphonous monoesters themselves are prepared from phosphonous dihalides by reaction with alcohols or by hydrolysis and subsequent esterification.

Functional phosphinic acids are obtained by reacting phosphonous dihalides (dihalophosphines) with activated olefinic compounds such as acrylic or methacrylic acid derivatives and then carrying out hydrolysis (Houben-Weyl, Volume 12/1, p. 230; K. K. Khairullin, T. I. Sobchuk, A. N. Pudovik, Zh. Obshch. Khim. 37, 710 (1967)). Byproducts produced are the halides of the organic acids used in the hydrolysis.

In addition, phosphonous dihalides can also be reacted with alkyl halides in the presence of aluminum chloride (Houben-Weyl, Volume 12/1, p. 232). Phosphinic esters can be prepared from phosphonous dialkyl esters by the Michaelis-Arbuzov reaction. Phosphonous dialkyl esters are in turn prepared from phosphonous dihalides and hydroxyl compounds.

The abovementioned phosphonous dihalides, e.g. methyldichlorophosphine, which can be used as starting materials for other syntheses, have been prepared themselves to date in a complex synthesis from phosphorus trihalides and alkyl halides in the presence of aluminum chloride (Houben-Weyl, Volume 12/1, p. 306). The reaction is highly exothermic and it can be managed industrially only with difficulty. In addition, various byproducts are formed which, as are also some of the abovementioned starting products, are toxic and/or corrosive, that is highly undesirable.

There is therefore a requirement for a process for preparing phosphinic esters, which process can be carried out in a simple manner and in which uniform products are obtained in a high yield. Such a process should also be considerably superior environmentally to those known hitherto.

SUMMARY OF THE INVENTION

The present invention relates to a process for preparing phosphinic esters and the use of the phosphinic esters prepared by this process.

The object therefore underlying the invention is to provide a process for preparing phosphinic esters, which process avoids the abovementioned disadvantages and starts from elemental yellow phosphorus as starting material.

This object is achieved by a process of the type described at the outset which comprises a) reacting elemental yellow phosphorus with alkyl halides in the presence of alkali metal hydroxide or alkaline earth metal hydroxide to form a mixture which comprises as main constituents the alkali metal salts and/or alkaline earth metal salts of alkylphosphonous acid, phosphorous acid and hypophosphorous acid b) removing the alkylphosphonous acid from the mixture obtained as described in a)

c) esterifying the alkylphosphonous acid d) adding the resultant ester of the alkylphosphonous acid to a compound having at least one C=C double bond.

The process according to the invention has considerable advantages in comparison with the previously known processes, since it avoids, inter alia, phosphonous dihalides as starting materials and also has a favorable balance in the product distribution.

DESCRIPTION OF THE PREFERRED EMBODIMENTS

Preferably, the alkyl halides are methyl chloride or methyl bromide.

Preferably, the reaction is carried out in step a) in a two-phase system of aqueous alkali metal hydroxide or alkaline earth metal hydroxide or mixtures thereof and an organic solvent.

Preferably, the organic solvents are unbranched or branched alkanes, alkyl-substituted aromatic solvents, water-immiscible or only partly water-miscible alcohols or ethers, alone or in combination with one another.

Particularly preferably, the organic solvent is toluene, alone or in combination with alcohols.

Preferably, the reaction is carried out in the presence of a phase-transfer catalyst.

Preferably, the phase-transfer catalyst is tetraalkylphosphonium halides, triphenylalkylphosphonium halides or tetraorganylammonium halides.

Preferably, the temperature in the reaction is from −20 to +60° C.

Particularly preferably, the temperature is from 0 to 30° C.

Preferably, the reaction is carried out at a pressure of from 0 to 10 bar.

Preferably, the process according to the invention is carried out in such a manner that the yellow phosphorus is suspended in a solvent or a solvent mixture and is then reacted with alkyl halide and a compound of the formula MOH or M'(OH)$_2$ or mixtures thereof, where M is an alkali metal and M' is an alkaline earth metal.

Preferably, the yellow phosphorus and the alkyl halide are reacted with one another in a molar ratio of from 1:1 to 1:3, the molar ratio of yellow phosphorus to the compound of the formula MOH or M'(OH)$_2$ being from 1:1 to 1:5.

Preferably, in step b) the alkylphosphonous acid is removed by distillation.

Preferably, in step c) esterification is performed by ethoxylation.

Preferably, for the ethoxylation as specified in step c), use is made of an oxirane such as ethylene oxide, propylene oxide or longer-chain oxiranes. Alternatively, use can also be made of ethylene carbonate. However, esterification can also be performed directly using an alcohol with elimination of water.

The phosphonous acid can be esterified to form the corresponding monoester, for example, by reaction with higher-boiling alcohols, with removal of the water formed by azeotropic distillation.

Suitable alcohols are, for example, butanol, hexanol, octanol, ethyl hexanol, ethylene glycol, diethylene glycol and/or glycerol.

Preferably, in step d), the addition is performed in the presence of catalysts.

These are preferably basic catalysts. Alternatively, acids or free-radical initiators can also be used.

Preferably, the basic catalysts are alkali metal alkoxides and/or alkaline earth metal alkoxides.

The compounds having at least one C=C double bond mentioned in step c) include, in particular, the olefins.

Preferably, the olefins are unbranched or branched α-olefins. Preferably the α-olefins are ethylene, n-, i-propylene, n-, i-butene, n-, i-pentene, n-, i-hexene, n-, i-octene, 1-decene, 1-dodecene, 1-tetradecene, 1-hexadecene, n-eicosene, and/or a mixture of 2,4,4-trimethylpentene isomers.

Suitable olefins are compounds of the formula $$\begin{array}{c} R^1 \\ R^2 \end{array} C = C \begin{array}{c} R^3 \\ R^4 \end{array}$$

where $R^1$–$R^4$ can be identical or different and are hydrogen, an alkyl group having from 1 to 18 carbon atoms, phenyl, benzyl or alkyl-substituted aromatics.

Also suitable are cycloolefins of the formula $$\bigcirc_{(CH_2)_n},$$

in particular cyclopentene, cyclohexene, cyclooctene and cyclodecene.

Use can also be made of open-chain dienes of the formula $$\begin{array}{c} R^5 \\ R^6 \end{array} C = C \begin{array}{c} R^7 \\ \end{array} - R^{11} - C \begin{array}{c} R^8 \\ \end{array} = C \begin{array}{c} R^9 \\ R^{10} \end{array}$$

where $R^5$–$R^{10}$ are identical or different and are hydrogen or a $C_1$ to $C_6$ alkyl group and $R^{11}$ is $(CH_2)$ n where n=0 to 6. Preference in this case is given to butadiene, isoprene and 1,5-hexadiene.

As cyclodienes, preference is given to 1,3-cyclopentadiene, dicyclopentadiene and 1,5-cyclooctadiene, and also norbornadiene.

Preferably, the olefins are those having an internal double bond, cyclic or open-chain dienes and/or polyenes having from 4 to 20 carbon atoms.

Preferably, the olefins bear a functional group.

Preferably, the olefins having functional groups are α,β-unsaturated carboxylic esters, carboxamides or carbonitriles, α, β-unsaturated ketones as well as alkyl vinyl sulfones and vinyl acetate.

Preferably, the olefins having functional groups are α,β-unsaturated carboxylic esters of aliphatic or cycloaliphatic alcohols having from 1 to 20 carbon atoms or carboxylic esters of polyhydric alcohols having 2 to 4 hydroxyl groups and 2 to 20 carbon atoms.

Preferably, the olefins having functional groups are acrylic acid derivatives of the formula (I), $$H_2C = C \begin{array}{c} R1 \\ | \\ \end{array} - C \begin{array}{c} O \\ \diagup\!\!\!\diagdown \\ R2 \end{array} \quad (I)$$

where R1 is $CH_3$ or H and R2 is an ester group of monohydric or polyhydric alcohols having 1–12 carbon atoms or an amine group.

Preferably, the olefins having functional groups are acrolein cyanohydrin compounds of the formula (II)

$$H_2C = HC - \begin{array}{c} O - R3 \\ | \\ CH \end{array} - CN \quad (II)$$

where R3=acetyl or propionyl.

Preferably, the olefins having functional groups are itaconic acid derivatives of the formula (III) where R'=alkyl group having 1–12 carbon atoms.

$$\begin{array}{c} H_2C - COOR' \\ | \\ H_2C = C - COOR' \end{array} \quad (III)$$

Preferably, the olefin having a functional group is hydroxyethyl acrylate, methyl acrylate, ethyl acrylate, hydroxyethyl methacrylate, methyl methacrylate, ethyl methacrylate, dimethyl itaconate, diethyl itaconate or acrolein cyanohydrin acetate.

Preferably, the olefin having a functional group is hydroxyethyl acrylate or hydroxyethyl methacrylate.

Preferably, the alkylphosphonous acid is methanephosphonous acid.

The invention also relates to the use of the phosphinic esters prepared by the process according to the invention as reactive flame retardants for polymers.

The invention also relates to the use of the phosphinic esters prepared by the process according to the invention as reactive flame retardants for thermoplastic polymers, such as polyethylene terephthalate, polybutylene terephthalate or polyamide.

The invention also relates to the use of the phosphinic esters prepared by the process according to the invention as reactive flame retardants for thermosetting resins, such as unsaturated polyester resins, epoxy resins, polyurethanes or acrylates.

The invention also relates to the use of the phosphinic esters prepared by the process according to the invention as precursors for the chemical synthesis of other phosphorus compounds.

The invention is illustrated by the examples below:

EXAMPLE 1
Reaction of yellow phosphorus with alkyl halide $$P_4 + CH_3Cl \xrightarrow{H_2O} H_3C-\underset{\underset{OH}{|}}{\overset{\overset{O}{\|}}{P}}-H$$

A 5 l stainless-steel pressure reactor is charged with 2 l of toluene, in which 25 g (0.05 mol) of tributylhexadecylphosphonium bromide have been previously dissolved, and preheated to 60° C. 62 g (2 mol) of molten yellow phosphorus are introduced into the reactor, cooled to 0° C. with vigorous stirring and then 202 g (4 mol) of methyl chloride are condensed in. In the course of 1 h, 1000 g of a solution of 600 g of KOH in 400 g of water are then introduced, the temperature being kept at 0° C. and the mixture being further reacted for 1 h at this temperature. The product mixture is heated to room temperature, diluted by 400 ml of water and the reactor is then expanded via an incineration stage.

Two phases are obtained. The aqueous phase comprises 64.2 mol % of methanephosphonous acid in the form of its potassium salt. After neutralization with hydrochloric acid, the methanephosphonous acid is distilled off in vacuo.

EXAMPLE 2
Ethoxylation of methanephosphonous acid $$H_3C-\underset{\underset{OH}{|}}{\overset{\overset{O}{\|}}{P}}-H \xrightarrow{H_2C-CH_2 \text{ (O)}} H_3C-\underset{\underset{OCH_2CH_2OH}{|}}{\overset{\overset{O}{\|}}{P}}-H$$

A 500 ml five-neck flask having a gas inlet tube, thermometer, intensive agitator and reflux condenser equipped with gas combustion is charged with 80.3 g (1 mol) methanephosphonous acid. Ethylene oxide is introduced at room temperature. A reaction temperature of 70° C. is set with stirring. After completion of ethylene oxide uptake, the mixture is allowed to react further at 80° C. for one hour. The ethylene oxide uptake is 65.7 g, corresponding to 1.5 mol. The acid number of the product is less than 1 mg of KOH/g. A colorless clear product is obtained. $^{31}$P-NMR: 38 ppm.

EXAMPLE 3
Addition of hydroxyethyl methanephosphonite to hydroxyethyl acrylate $$H_3C-\underset{\underset{OCH_2CH_2OH}{|}}{\overset{\overset{O}{\|}}{P}}-H +$$

$$H_2C=CH-\overset{\overset{O}{\nearrow}}{C}_{O-CH_2-H_2C-OH} \longrightarrow$$

$$H_3C-\underset{\underset{OCH_2CH_2OH}{|}}{\overset{\overset{O}{\|}}{P}}-CH_2CH_2-\overset{\overset{O}{\nearrow}}{C}_{O-CH_2-H_2C-OH}$$

A 500 ml five-neck flask equipped with thermometer, reflux condenser, intensive agitator and dropping funnel is charged with 67 g (0.46 mol) of hydroxyethyl methanephosphonite and 53.2 g of hydroxyethyl acrylate. 25 ml of sodium methoxide (30%) are added dropwise thereto, with stirring, at a rate such that a reaction temperature of 60° C. is established. The mixture is then allowed to react further at 80° C. for 10 min. A pale yellow liquid is obtained. The phosphorus content is 11.0%, the carbon content 40.3% and the hydroxyl number is 148 mg/g. $^{31}$P-NMR (CHCl$_3$): 64 ppm.

EXAMPLE 4
Addition of hydroxyethyl methanephosphonite to acrylamide

A 500 ml five-neck flask equipped with thermometer, reflux condenser, intensive agitator and dropping funnel is charged with 65 g (0.445 mol) of hydroxyethyl methanephosphonite and 31.6 g of acrylamide. 40 ml of sodium methoxide (30%) are added dropwise, with stirring, at a rate such that a reaction temperature of 80° C. is set. The mixture is then reacted for a further 10 min at 80° C. A pale yellow liquid is obtained. $^{31}$P-NMR (CHCl$_3$): 55 ppm.

EXAMPLE 5
Addition of hydroxyethyl methanephosphonite to acrylonitrile

A 500 ml five-neck flask equipped with thermometer, reflux condenser, intensive agitator and dropping funnel is charged with 81.6 g (0.559 mol) of hydroxyethyl methanephosphonite and 37.4 g of acrylonitrile. 40 ml of sodium methoxide (30%) are added dropwise, with stirring, at a rate such that a reaction temperature of 70° C. is established. The mixture is then allowed to react for a further 10 min at 80° C. A pale yellow liquid is obtained. $^{31}$P-NMR (CHCl$_3$): 53–54 ppm.

EXAMPLE 6
Addition of hydroxyethyl methanephosphonite to methyl acrylate

A 500 ml five-neck flask equipped with thermometer, reflux condenser, intensive agitator and dropping funnel is charged with 73 g (0.445 mol) of hydroxyethyl methanephosphonite and 43 g of methyl acrylate. 40 ml of sodium methoxide (30%) are added dropwise, with stirring, at a rate such that a reaction temperature of 80° C. is established.

A pale yellow liquid is obtained. $^{31}$P-NMR (CHCl$_3$): 58 ppm.

EXAMPLE 7
Addition of hydroxyethyl methanephosphonite to dimethyl itaconate

A 500 ml five-neck flask equipped with thermometer, reflux condenser, intensive agitator and dropping funnel is charged with 43.8 g (0.3 mol) of hydroxyethyl methanephosphonite and 47.4 g of dimethyl itaconate (0.3 mol). 3 ml of sodium methoxide (30%) are added dropwise, with stirring, at a rate such that a max. reaction temperature of 90° C. is established. The mixture is then allowed to react for a further 1 h at 50–70° C.

A pale yellow liquid is obtained. $^{31}$P-NMR (CHCl$_3$): 55–56 ppm.

EXAMPLE 8
Reaction of methanephosphonous acid with n-butanol

A 250 ml three-neck flask equipped with thermometer, water separator and intensive agitator is charged with 43.8 g (0.3 mol) of hydroxyethyl methanephosphonite and 37.1 g of n-butanol (0.5 mol). At a reaction temperature of 90–110° C., the water formed is removed by azeotropic distillation. The product is then purified by distillation at 1 mbar.

EXAMPLE 9
Reaction of methanephosphonous acid with sobutanol

A 250 ml three-neck flask equipped with thermometer, water separator and intensive agitator is charged with 43.8 g (0.3 mol) of hydroxyethyl methanephosphonite and 37.1 g of isobutanol (0.5 mol). At a reaction temperature of 80–110° C., the water formed is removed by azeotropic distillation. The product is then purified by distillation at 1 mbar.

EXAMPLE 10
Addition of isobutyl methanephosphonite to acrolein cyanohydrin acetate A 500 ml five-neck flask equipped with thermometer, reflux condenser, intensive agitator and dropping funnel is charged with 110 g of isobutyl methanephosphonite. In the course of one hour, with stirring, at 130° C., 50 g of acrolein cyanohydrin acetate and 4 g of t-butyl peroctoate are added dropwise. The mixture is then allowed to react for a further 15 min at 120° C. and the product is then distilled off in a high vacuum at 170° C. and 0.4 mbar.

94 g of isobutyl 3-(acetoxy-3-cyanopropyl)-methylphosphinate are obtained, equivalent to a yield of 89.5% of theory.

EXAMPLE 11
Addition of isobutyl methanephosphonite to acroleincyanohydrin propionate A 500 ml five-neck flask equipped with thermometer, reflux condenser, intensive agitator and dropping funnel is charged with 110 g of isobutyl methanephosphonite. In the course of one hour, 50 g of acroleincyanohydrin propionate and 4 g of t-butyl peroctoate are added dropwise with stirring at 130° C. The mixture is then allowed to react for a further 15 min at 120° C. and the product is then distilled off in a high vacuum at 180° C. and 0.4 mbar.

94 g of isobutyl 3-(acetoxy-3-cyanopropyl)-methylphosphinate are obtained, equivalent to a yield of 84.5% of theory.

What is claimed is:

1. A process for preparing phosphinic esters which comprises
   a) reacting elemental yellow phosphorus with alkyl halides in the presence of alkali metal hydroxide or alkaline earth metal hydroxide to form a mixture which comprises as main constituents the alkali metal salts and/or alkaline earth metal salts of alkylphosphonous acid, phosphorous acid and hypophosphorous acid
   b) removing the alkylphosphonous acid from the mixture obtained as described in a),
   c) esterifying the alkylphosphonous acid,
   d) adding the resultant ester of the alkylphosphonous acid to a compound having at least one C=C double bond.

2. The process as claimed in claim 1, wherein the alkyl halides used are methyl chloride or methyl bromide.

3. The process as claimed in claim 1, wherein the reaction is carried out in an organic solvent.

4. The process as claimed in claim 3, wherein the organic solvent is selected from unbranched or branched alkanes, alkyl-substituted aromatic solvents, water-immiscible or only partly water-miscible alcohols or ethers, alone or in combination with one another.

5. The process as claimed in claim 4, wherein the organic solvent is toluene, alone or in combination with alcohols.

6. The process as claimed in claim 1, wherein the reaction is carried out in the presence of a phase-transfer catalyst.

7. The process as claimed in claim 6, wherein the phase-transfer catalyst is selected from tetraalkylphosphonium halides, triphenylalkylphosphonium halides or tetraorganylammonium halides.

8. The process as claimed in claim 1, wherein the temperature in the reaction is –20 to +60° C.

9. The process as claimed in claim 1, wherein the temperature is from 0 to 30° C.

10. The process as claimed in claim 1, wherein the reaction is carried out at a pressure of from 0 to 10 bar.

11. The process as claimed in claim 1, wherein the yellow phosphorus is suspended in a solvent or a solvent mixture and is then reacted with an alkyl halide and a compound of the formula MOH or M'(OH)$_2$ or mixtures thereof, where M is an alkali metal and M' is an alkaline earth metal.

12. The process as claimed in claim 1, wherein the yellow phosphorus and the alkyl halide are reacted with one another in a molar ratio of from 1:1 to 1:3, the molar ratio of yellow phosphorus to the compound of the formula MOH or M'(OH)$_2$ being from 1:1 to 1:5.

13. The process as claimed in claim 1, wherein, in step b), the alkylphosphonous acid is removed by distillation.

14. The process as claimed in claim 1, wherein, in step c), esterification is performed by ethoxylation.

15. The process as claimed in claim 1, wherein, in step c), esterification is performed directly by reaction with alcohols with elimination of water.

16. The process as claimed in claim 1, wherein, in step d), addition is performed in the presence of catalysts.

17. The process as claimed in claim 16, wherein the catalysts are basic catalysts.

18. The process as claimed in claim 16, wherein the basic catalysts are alkali metal alkoxides and/or alkaline earth metal alkoxides.

19. The process as claimed in claim 1, wherein the compounds having at least one C=C double bond are olefins.

20. The process as claimed in claim 19, wherein the olefins are olefins having functional groups.

21. The process as claimed in claim 20, wherein the olefins having functional groups are α,β-unsaturated carboxylic esters, carboxylic acid chlorides, carboxamides or carbonitriles, α,β-unsaturated ketones as well as alkyl vinyl sulfones and vinyl carboxylates.

22. The process as claimed in claim 21, wherein the olefins having functional groups are α,β-unsaturated carboxylic esters of aliphatic or cycloaliphatic alcohols having from 1 to 20 carbon atoms or are carboxylic esters of polyhydric alcohols having from 2 to 4 hydroxyl groups and from 2 to 20 carbon atoms.

23. The process as claimed in claim 1, wherein the olefins having functional groups are acrylic acid derivatives according to the formula (I),

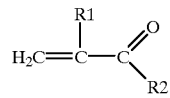

where R1 is CH$_3$ or H and R2 is an ester group of monohydric or polyhydric alcohols having 1–12 carbon atoms or an amine group.

24. The process as claimed in claim 1, wherein the olefins having functional groups are acroleincyanohydrin compounds according to formula (II)

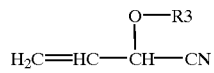

where R3=acetyl or propionyl.

25. The process as claimed in claim 1, wherein the olefins having functional groups are itaconic acid derivatives of the formula (III) where R'=alkyl group having 1–12 carbon atoms.

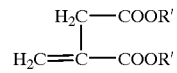

26. The process as claimed in claim 1, wherein the olefin is hydroxyethyl acrylate, methyl acrylate, ethyl acrylate, hydroxyethyl methacrylate, methyl methacrylate, ethyl methacrylate, dimethyl itaconate, diethyl itaconate or acrolein cyanohydrin acetate.

27. The process as claimed in claim 1, wherein the alkylphosphonous acid is methanephosphonous acid.

* * * * *